United States Patent [19]
Glaesemann et al.

[11] Patent Number: 5,076,104
[45] Date of Patent: Dec. 31, 1991

[54] METHOD FOR MEASURING ACTUAL LOAD AT FAILURE OF OPTICAL FIBER

[75] Inventors: G. Scott Glaesemann, Corning; Dale R. Powers; Donald J. Walter, both of Painted Post, all of N.Y.

[73] Assignee: Corning Incorporated, Corning, N.Y.

[21] Appl. No.: 607,723

[22] Filed: Nov. 1, 1990

[51] Int. Cl.$^5$ .............................................. G01N 3/02
[52] U.S. Cl. ......................................................... 73/830
[58] Field of Search .................. 73/830, 828, 160, 829

[56] References Cited

U.S. PATENT DOCUMENTS

| 4,601,208 | 7/1986 | McKay et al. | 73/829 |
| 4,825,702 | 5/1989 | Cizek | 73/828 |

FOREIGN PATENT DOCUMENTS

| 152587 | 7/1953 | Australia | 73/830 |
| 253425 | 2/1970 | U.S.S.R. | 73/830 |

OTHER PUBLICATIONS

Jackson, L. A. et al., A Technique for . . . Optical Fibers, J. Phys. E: Sci. Instrum., vol. 11, No. 2, Feb. '78, pp. 161-165.

*Primary Examiner*—Jerry W. Myracle
*Attorney, Agent, or Firm*—K. McNeill Taylor, Jr.

[57] ABSTRACT

Method and apparatus wherein continuous indexed lengths of optical fiber are automatically measured for load at failure for each failure below a predetermined maximum stress. A predetermined length of optical fiber is indexed. The optical fiber is clamped at one or more clamp points along its length. Increasing tension is applied to a first indexed length of optical fiber between at least one clamp point and a tension application means. Increasing tension is applied between an initial value and the predetermined maximum load. The increasing tension is measured during its application. If failure occurs, the actual load at failure is detected while the increasing tension is being applied. When failure does not occur, the first length of optical fiber is released and a second length of optical fiber is indexed to the position where increasing tension is applied to the second length between at least one clamp point and the tension application means.

7 Claims, 4 Drawing Sheets

METHOD FOR MEASURING ACTUAL LOAD AT FAILURE OF OPTICAL FIBER

BACKGROUND OF THE INVENTION

This invention relates to a method for characterizing the low end of the strength distribution for many kilometers of optical fiber in a relatively short period of time.

Measurement capabilities for optical fiber are well know. Testing of optical fiber falls into three categories: 1) optical properties, including total attenuation and loss; 2) mechanical parameters, including optical fiber size and core/cladding dimensions; and 3) optical fiber strength related properties.

Typically, the long term reliability of optical fiber depends on the strength of the glass. The strength of glass is controlled by the presence of cracks and flaws. Strong glass optical fibers may be easily damaged and their strength greatly reduced by the introduction of cracks. Cracks can be produced by chemical or mechanical means. The presence of cracks cause breakage of the glass optical fiber at a given stress. Therefore, to assess their reliability, glass optical fibers must be strength tested by applying tension to detect cracks and flaws.

Manufacturers of optical fiber usually proof test optical fibers in the plant. Proof testing optical fiber yields data to monitor the production process and gauge product improvement. However, customers may require proof testing of optical fiber to ensure that all spooled optical fibers have a strength above a minimum level necessary to handle safely without breaks. This level is set at a value, such as 50 or 100 kpsi, at which there is a reasonable probability of testing complete multi-kilometer lengths.

U.S. Pat. No. 4,148,218, issued on Apr. 10, 1979 to Knowles et al. discloses an apparatus for strength testing optical fiber. This apparatus applies a preset tension to a continuous length of optical fiber so that any flaws which result in a strength less than the preset tension will be detected by optical fiber breakage. First and second tractor assemblies are used to apply the preset tension to the optical fiber. The optical fiber is threaded into the first tractor assembly as it exits the furnace or alternatively from reels of previously drawn optical fiber. The Knowles et al. apparatus is capable of testing relatively long lengths of optical fiber, but is seriously deficient in that it is not practical for determining the actual load at failure for a range of strengths.

Static fatigue test equipment exists in the prior art. Static fatigue is time dependent, in the sense that failure will eventually occur, provided the stress exceeds some minimal value. One example of a prior art static fatigue tester requires loading a constant weight to a length of optical fiber. The weight strains the optical fiber until it breaks after a period of time. This type of device is limited in the number of optical fiber lengths that can be tested at a given time. A significant problem with this type of testing is that every length of optical fiber must be tested to destruction. Another drawback is the difficulty of testing multi-kilometer lengths in a short period of time. Testing of kilometer lengths of optical fiber over periods of years is impractical.

An example of a prior art dynamic fatigue tester involves applying an increasing tension to an individual length of optical fiber. The increasing tension is applied until the optical fiber breaks, recording an actual load at failure. Some of these testers are environmentally controlled (temperature and/or humidity). Both of the previously disclosed testers require time consuming set up and loading. For a general discussion of static and dynamic fatigue testers, see Kalish and Tariyal, "Static and Dynamic Fatigue of A Polymer-Coated Fused Silica Optical Fiber," Journal of American Ceramic Society, Vol. 61. No. 11-12, Nov. -Dec. 1978, pp 518-523.

The prior art testers identified above are particularly instructive to the extent that they appear to reflect a failure by the prior art to conceive of an apparatus to continuously strength test optical fiber. Prior art testers are unable to measure the distribution of strength of only the low strength breaks. Thus, one attribute of the present invention is that, in the preferred embodiment thereof, a method and an apparatus is provided which is particularly adapted to the task of automatically testing reels of optical fiber and detecting the actual load at failure of lower strength breaks.

It is therefore an object of the present invention to provide an apparatus for applying increasing tension to incremental lengths of an optical fiber.

Another object of the present invention to provide an apparatus for automatically indexing lengths of optical fiber.

It is another object of the present invention to apply increasing tension to an optical fiber to establish the complete range of actual strength values for a length of optical fiber.

It is another object of the present invention to provide an apparatus for measuring load at failure without destroying all of the optical fiber.

SUMMARY OF THE INVENTION

In accordance with the present invention, continuous indexed lengths of optical fiber are automatically measured for load at failure for each failure below a predetermined maximum stress.

In one embodiment of the present invention, a method of testing optical fiber to detect load at failure for each break below a predetermined maximum load is provided. A predetermined length of optical fiber is indexed. The optical fiber is clamped at one or more clamp points along its length. Increasing tension is applied to a first indexed length of optical fiber between at least one clamp point and a tension application means. Increasing tension is applied between an initial value and the predetermined maximum load. The increasing tension is measured during its application. If failure occurs, the actual load at failure is detected while the increasing tension is being applied. When failure does not occur, the first length of optical fiber is released and a second length of optical fiber is indexed to the position where increasing tension is applied to the second length between at least one clamp point and the tension application means.

In another embodiment of the present invention an apparatus for testing optical fiber to detect load at failure for each break below a predetermined maximum load is provided. A first length of optical fiber is indexed from a payout reel. A first tractor assembly, including at least a first wheel, receives the optical fiber from the payout reel. The first length of optical fiber is clamped within the first wheel. A second tractor assembly, including at least a second wheel, receives the first length of optical fiber from the first tractor assembly.

The first length of optical fiber is clamped within the second wheel. A load cell is reciprocally mounted to receive the first length of optical fiber from the second tractor assembly. The tension applied to the first length of optical fiber is increased. The tension is applied to the first length of optical fiber between the first wheel and the second wheel. The increasing tension is applied between an initial value and a predetermined maximum load.

After inspection, the first length of optical fiber is wound onto a takeup reel. A second length of optical fiber is indexed to a position where increasing tension may be applied between the first wheel and the second wheel.

In an alternative embodiment, the load cell is stationary and increasing tension is supplied by rotating one or more capstans.

In an alternative embodiment of the present invention, the conventional screener is replaced by a simpler set of capstans.

DETAILED DESCRIPTION OF THE INVENTION

Figure 1:
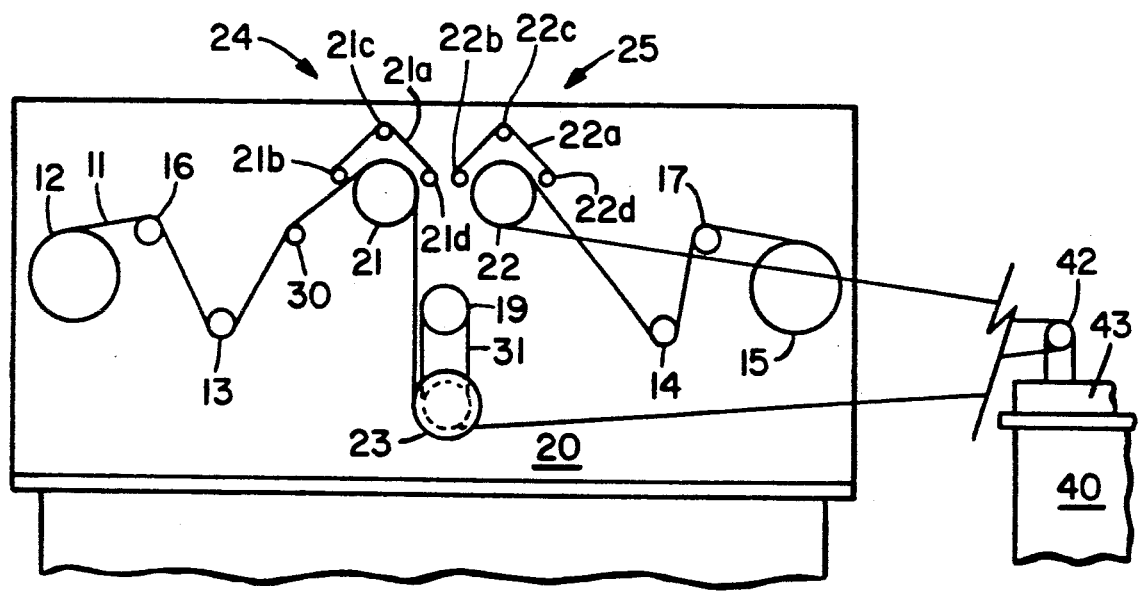
FIG. 1 is a simplified front view of one embodiment of the present invention.

Referring to FIG. 1 there is shown a front view of an apparatus embodiment of our invention. The apparatus shown in FIG. 1 includes a frame 20. Extending outwardly from frame 20 are two shafts, not shown, affixed at opposite ends of frame 20, to support payout reel 12 and takeup reel 15. Also, attached to frame 20 is a first tractor assembly 24 and a second tractor assembly 25.

The first tractor assembly 24 includes tractor wheel 21 rotatively mounted to frame 20. Tractor wheel 21 is rotated in a clockwise direction by a motor or other conventional means, not shown. Partially encircling and extending upwardly from tractor wheel 21 is belt 21a surrounding three idler wheels 21b, 21c, and 21d in a triangular configuration. Belt 21a held in tension by springs (not shown) attached to idler wheels. Belt 21a rotates in a clockwise direction as tractor wheel 21 rotates. Tractor wheel 21 is arranged so that optical fiber 11 contacts its periphery and maybe clamped throughout the arc created by belt 21a by locking wheel 21 in place.

The second tractor assembly 25 is similar to the first. It includes a tractor wheel 22, belt wheels 22b, 22c, and 22d, and belt 22a. Tractor wheels 21 and 22 rotate at the same speed to transport optical fiber 11 along a path in which optical fiber 11 is bent over the surface of the wheels.

Optical fiber 11 is introduced into the junction between belt 21a and tractor wheel 21 from payout reel 12. The optical fiber 11 passes from payout reel 12 around idler wheel 16, dancer 13, and idler wheel 30 to the first tractor assembly 24. Idler wheels 16 and 30 guide optical fiber 11. Idler wheel 30 is positioned to center optical fiber 11 around tractor wheel 21.

Dancer 13 moves upwardly and downwardly to adjust the slack of optical fiber 11 from payout reel 12 in response to the speed of tractor wheel 21, especially when payout reel 12 and tractor wheel 21 rotational speeds are not synchronous.

Optical fiber 11 passes through the first tractor assembly 24 through an open space and around grooved wheel 19 and grooved dancer 23. Grooved wheel 19 is fixedly secured to frame 20 and grooved dancer 23 is mounted for vertical movement on frame 20. Optical fiber 11 is looped around wheel 19 and dancer 23. A weight, not shown, of approximate 410 grams is hung from dancer 23, maintaining a constant tension on optical fiber 11. The constant tension on optical fiber 11 provided by the weight is to control any unnecessary slack found on the indexed length of optical fiber 11. Optical fiber 11 passes from dancer 23 to tension stand assembly 40.

Tension stand assembly 40 is further described in connection with FIGS. 2 and 3. Tension stand assembly 40 includes a base 46 and tension slide 43 mounted onto base 46. Load cell 41 is mounted to a carrier bracket 47 for reciprocating movement along tension slide 43. Tension slide 43 is a TOL-O-MATIC band cylinder (rodless cylinder) with a 1¼ inch bore. Located within tension slide 43 is a piston, and a steel bracket connects the piston to the carrier bracket 47. Tension slide 43 contains two limit switches to control the stroke and reset the control in the event of fiber break. A cushion at each end of tension slide 43 provides for a smooth deceleration at the end of full strokes. The cylinder is fed by filtered and lubricated air regulated to about 50 psi. The piston moves within the cylinder as it is pressurized.

Pulley 42 is mounted on the face of load cell 41 via two ball bearings, not shown, on the center post at a precise distance from the load cell 41. Rubber mounts 45 are attached to the bottom of base 46 and aid in vibration dampening. Safety shield 44 is mounted onto base 46 at the rear of tension slide 43 as a precautionary measure when optical fiber 11 breaks.

Pulley 42 receives optical fiber 11 from dancer 23. Optical fiber 11 passes to the second tractor assembly 25 and is clamped between belt 22a and tractor wheel 22 throughout the arc created by belt 22a. Optical fiber 11 passes through the second tractor assembly 25 through an open space, around dancer 14, and around idler wheel 17 to takeup reel 15. Idler wheel 17 guides optical fiber 11. Dancer 14 moves upwardly and downwardly to adjust the slack of optical fiber 11 from tractor assembly 25 to takeup reel 15.

Load cell 41 applies an increasing tension to the length of optical fiber 11 clamped at the points between the first and second tractor assembly. The load cell 41 moves in a reciprocating movement along the tension slide applying tension to optical fiber 11 from an initial value to a predetermined maximum load. Load cell 41 experiences approximately twice the load experienced by the lengths of optical fiber 11 spanning between first tractor assembly 24 and second tractor assembly 25. For example, a 20 pound maximum load in the load cell translates to approximately 10 pounds on each length of optical fiber 11.

If the length of optical fiber 11 does not break when the tension from load cell 41 is applied, a new length of optical fiber is indexed. The first length is wound onto takeup reel 15. The second length follows the path discussed above, is clamped at the first and second tractor assemblies and increasing tension is applied from load cell 41. After each application of tension, optical fiber 11 is indexed from payout reel 12 until the reel is empty.

Figure 2:
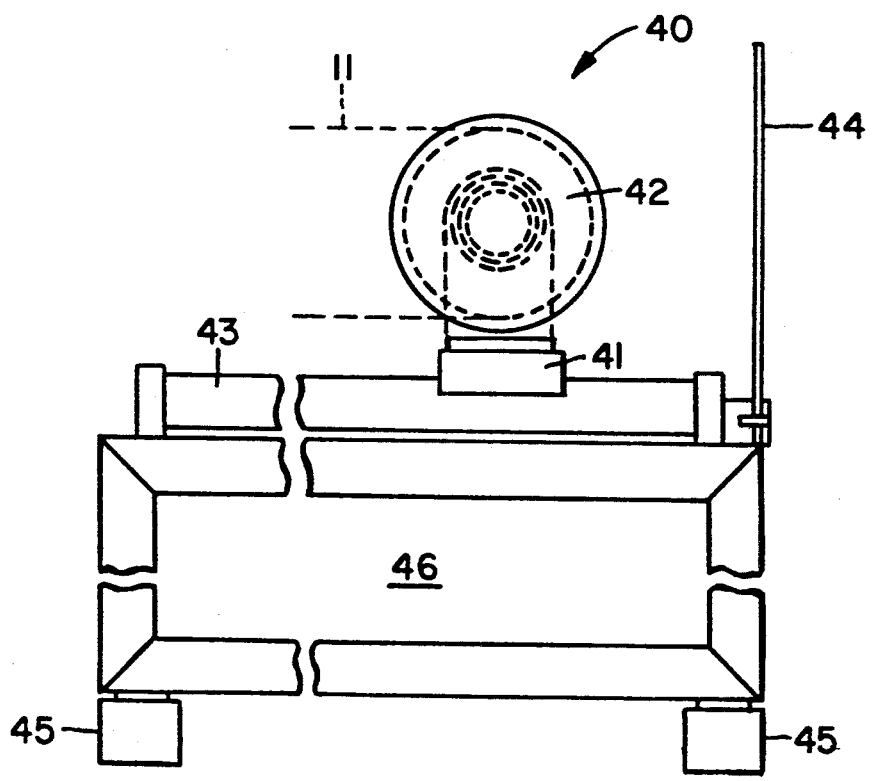
FIG. 2 is a front view of the tension stand assembly.
Figure 3:
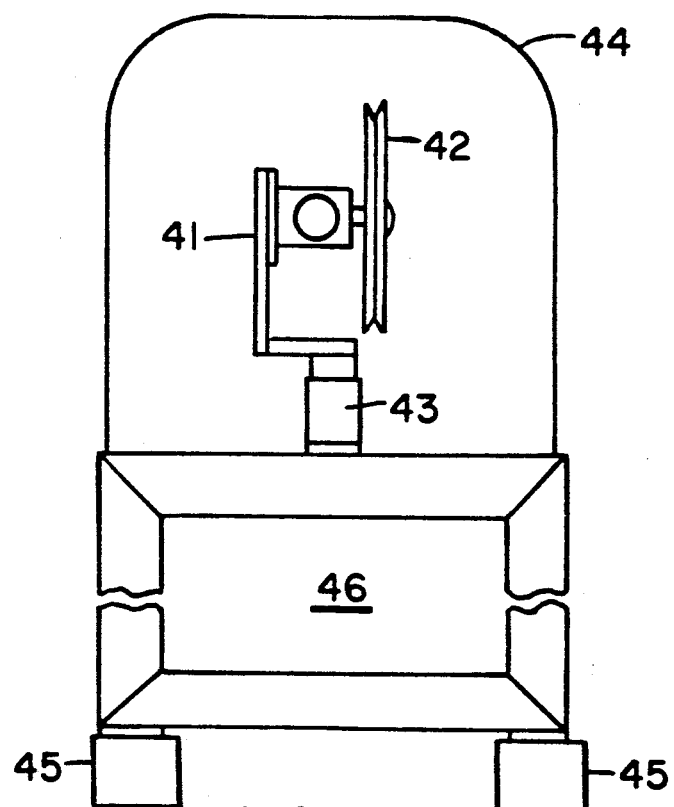
FIG. 3 is a side view of FIG. 2.

In view of the foregoing description of the apparatus components shown in FIGS. 1, 2, and 3, the operation of the apparatus may now be understood. A twenty meter length of optical fiber 11 is fed into tractor assembly 24, around load cell 41, and returned to tractor assembly 25. Optical fiber 11 is clamped in the arc created by the tractor wheel 21, and belt 21a, by locking wheels 21 in place. Optical fiber 11 is clamped in the arc created by the tractor wheel 22 and belt 22a, by locking wheels 22 in place. By this mechanism, belts 21a, 22a remain stationary as optical fiber 11 is not moving. The lower portion of belts 21a, 22a apply relatively constant pressure against their respective tractor wheel and the portion of optical fiber 11 between the belt and the wheel. Conventional signal generating means may be supplied to detect the presence of optical fiber 11 in a position around load cell 41. When the presence of optical fiber 11 has thus been detected, load cell 41 is actuated, thereby moving rearwardly along tension slide 43. During rearward movement of load cell 41, it may again be observed that optical fiber 11 remains clamped throughout the arc created at first and second tractor assemblies 24 and 25.

As load cell 41 moves rearwardly, a displaying-/recording device displays the load applied to optical fiber 11. Fiber tension increases as the load cell moves rearwardly. As it leaves its home position, the load is some minimal value corresponding to the weight hung from dancer 23. Tension increases to a predetermined maximum value as the load cell moves. In this manner, increasing tension is applied to optical fiber 11 in the indexed length between tractor assembly 24 and tractor assembly 25. At the end of the rearward movement, tension is released by returning load cell 41 to its home position.

At this point in the sequence, the indexed length of optical fiber has been cycled, and an increasing tension has been applied. Thereupon, in response to a signal from appropriate and conventional control means, wheel 21 and 22 are free to rotate and optical fiber 11 is no longer clamped. The cycled length of optical fiber is wound onto takeup reel 15 and a new length of optical fiber 11 is indexed from payout reel 12.

Returning to FIG. 2, it should be noted that in the case where optical fiber 11 fails due to the increasing tension applied by load cell 41, load cell 41 continues its rearward movement to its furthest position along tension slide 43. The actual load at failure is held in memory and displayed on the displaying/recording device.

As indicated earlier, control of the various operations performed by the present invention shown in FIG. 1 may be realized by employing any conventional programming or sequencing means known to those skilled in the art to which this invention pertains.

The embodiment shown in FIG. 1 facilitates easy threading; the technique required is similar to prior art screeners or proof testers.

Alternative embodiments of the invention are shown in more detail in FIGS. 4-7. Like reference numerals are used to denote like parts. The drawings are not intended to indicate scale or relative proportions of the elements shown therein.

Figure 4:
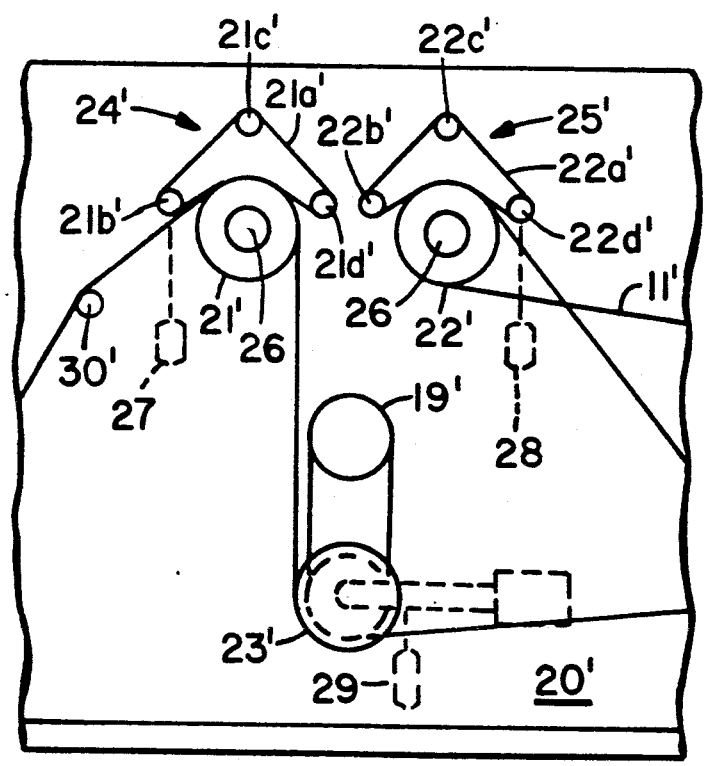
FIG. 4 is an alternative screener incorporated in one embodiment of the present invention.

Reference is now made to FIG. 4 for a detailed description of the first tractor assembly 24' and second tractor assembly 25' mounted onto frame 20. Brake means 26 are added to first and second tractor assembly to clamp optical fiber 11 during the fiber tensioning cycle. Brake means 26 also hold tractors wheels 21' and 22' in place. As brake means 26 is applied to tractor wheels 21',22', belts 21a',22a' remain stationary and press the fiber against wheels 21' and 22'.

FIG. 4 shows a modification of tractor assemblies in which weight 27 is connected to tractor assembly 24' and weight 28 is connected to tractor assembly 25'. The need for the weight addition was to increase the friction force on the optical fiber. The optical fiber would otherwise pull through the friction lock comprised of the wheel and belt configuration of the tractor assemblies. If optical fiber 11 slides over tractor wheel 21' or 22', the fiber surfaces will be abraded resulting in considerable loss in strength.

FIG. 4 shows a modification to dancer 23' in which the weight 29 is connected to dancer 23 to keep a constant tension on optical fiber 11 during payout from payout reel 12. Weight 29 is hung from arm 32 extending outwardly from the rear of dancer 23.

Figure 5:
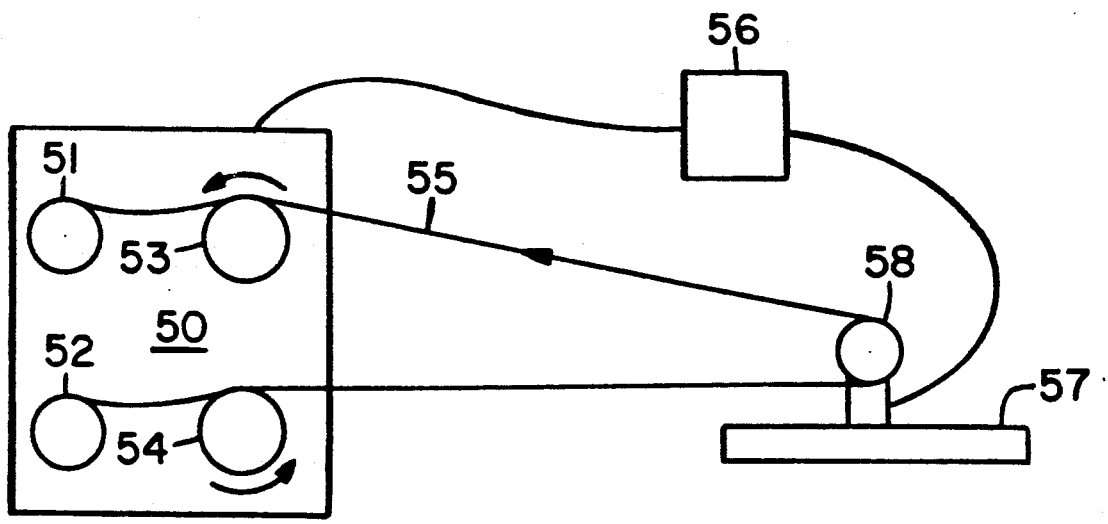
FIG. 5 is a schematic of an alternative embodiment of the present invention.

FIG. 5 depicts an alternative embodiment of the present invention. In this embodiment, optical fiber 55 is wound at a constant tension about a first capstan 54 and a second capstan 53 and clamped in place by means of the friction between the wound fiber and the capstan surfaces. Tension is applied by payout reel 52 and takeup reel 51 to maintain this friction. Load cell 58 applies increasing tension to optical fiber 55.

The load cell 58 moves in a reciprocating movement along the tension slide 57 applying tension to optical fiber 55 from an initial value to a predetermined maximum load, similar to load cell 41 depicted in FIGS. 2 and 3. This embodiment of the invention has the advantage that very little excessive force is applied to the optical fiber. The optical fiber is not pressed between two surfaces wherein the fiber surfaces may be abraded resulting in considerable loss in strength.

If the length of optical fiber 55 does not break when the tension from load cell 58 is applied, a new length of optical fiber is indexed. Optical fiber 55 is indexed from payout reel 52 until the reel is empty. The lengths of optical fiber 55 are wound onto takeup reel 51. Conventional control 56 sends relay signals to takeup reel 51, capstans 53 and 54, mounted onto frame 50 and load cell 58 to index new lengths of optical fiber 55 and move load cell 58 along tension slide 57.

Figure 6:
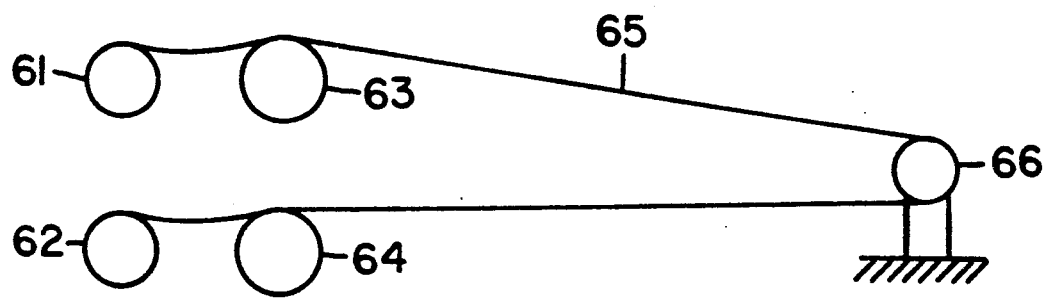
FIG. 6 is a schematic of an alternative embodiment of the present invention.
Figure 7:
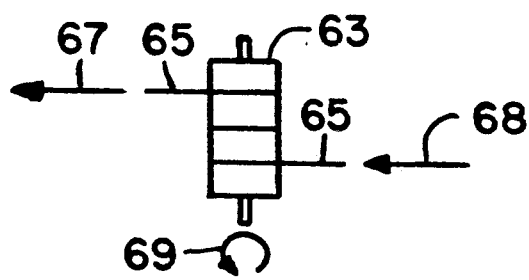
FIG. 7 is a schematic of capstan 63 illustrated in FIG. 6.

Clamping in this embodiment and in the embodiment depicted in FIGS. 6 and 7 does not require an additional surface for pressing against optical fiber 55 such as that provided by belts 21a and 22a.

Referring to FIGS. 6 and 7, a capstan 63 is rotated in the direction of arrow 69 to increase tension on optical fiber 65 to a predetermined load as indicated on stationary load cell 66. Optical fiber 65 extends from payout reel 62 about a first capstan 64 and around stationary load cell 66. Optical fiber 65 is clamped in place around capstan 64 by means of the friction between the wound fiber and the capstan surface. Tension is applied by payout reel 62 to maintain the friction on first capstan 64. The tension applied by capstan 63 is increased by rotating capstan 63 to wrap the fiber around capstan 63.

Tension is applied by takeup reel 61 to maintain the friction between the surface of capstan 63 and the wound fiber. Arrow 60 represents the direction of movement of optical fiber 65 from the load cell. Arrow 67 represents the direction of movement of optical fiber 65 to takeup reel 61. Takeup reel 61 is rotated at a speed to takeup the excess optical fiber 65 as it elongates and to maintain the desired tension applied by rotating capstan 63. In an alternative embodiment, the increasing tension may be applied by simultaneous rotation of capstans 63 and 64 in the same direction.

EXAMPLE

A specific example of an apparatus for measuring actual load at failure in optical fiber is now described with reference to FIG. 1. A screener/re-winder 20 from Sterling Davis Electric, Wallingford, Connecticut was used. The screener 20 was modified to pay out 20 meters of optical fiber 11 automatically from the payout reel 12, around pulley 42 and back to the takeup reel 15.

Any physical load was removed from the load cell. A signal conditioner from Sensotec Corporation, Columbus, Ohio was provided to convert the load cell's electric signals to a digital format. Prior to payout load cell 41 was checked to ensure the display provided by the signal conditioner was accurate.

A tension stand assembly 40 comprising a frame 46, a baseplate, and a pneumatic slide 43 attached to the baseplate was provided. A load cell 41 from A. L. Design, Inc., Amherst New York was provided. A pulley 42 was mounted on the face of the load cell 41. The load cell 41 and pulley 42 configuration was placed to slide along the tension slide 43. The load cell 41 was moved along the tension slide 43 in the direction of the screener 20, causing the load cell 41 to return to its home position to begin tension cycling.

The gauge length counter on the screener 20 was set to the desired length, 20 meters. The total optical fiber length counter on the screener 20 was reset to zero. A reel of 24 kilometers was loaded onto the spindle and threaded through the screener 20 around idler wheel 16, dancer 13, idler wheel 30, and into the first tractor assembly 24.

Screener speed was brought to twenty percent of the maximum rotational speed of tractor wheel 21 and turned on, allowing an operator to manually thread the optical fiber 11 through the remaining elements. An operator walked the optical fiber to the load cell 41 around the pulley 42 and back to the screener 20. While standing in front of the screener, keeping tension on the optical fiber 11, approximately six feet of excess optical fiber 11 was payed out and the screener speed was turned off. The excess optical fiber 11 was threaded around a second tractor assembly 25, under a dancer 14, and around the top of idler wheel 17, and secured to the takeup reel 15. Optical fiber 11 was clamped within the arc of each tractor assembly created by the tractor wheel and the belt.

Figure 8:
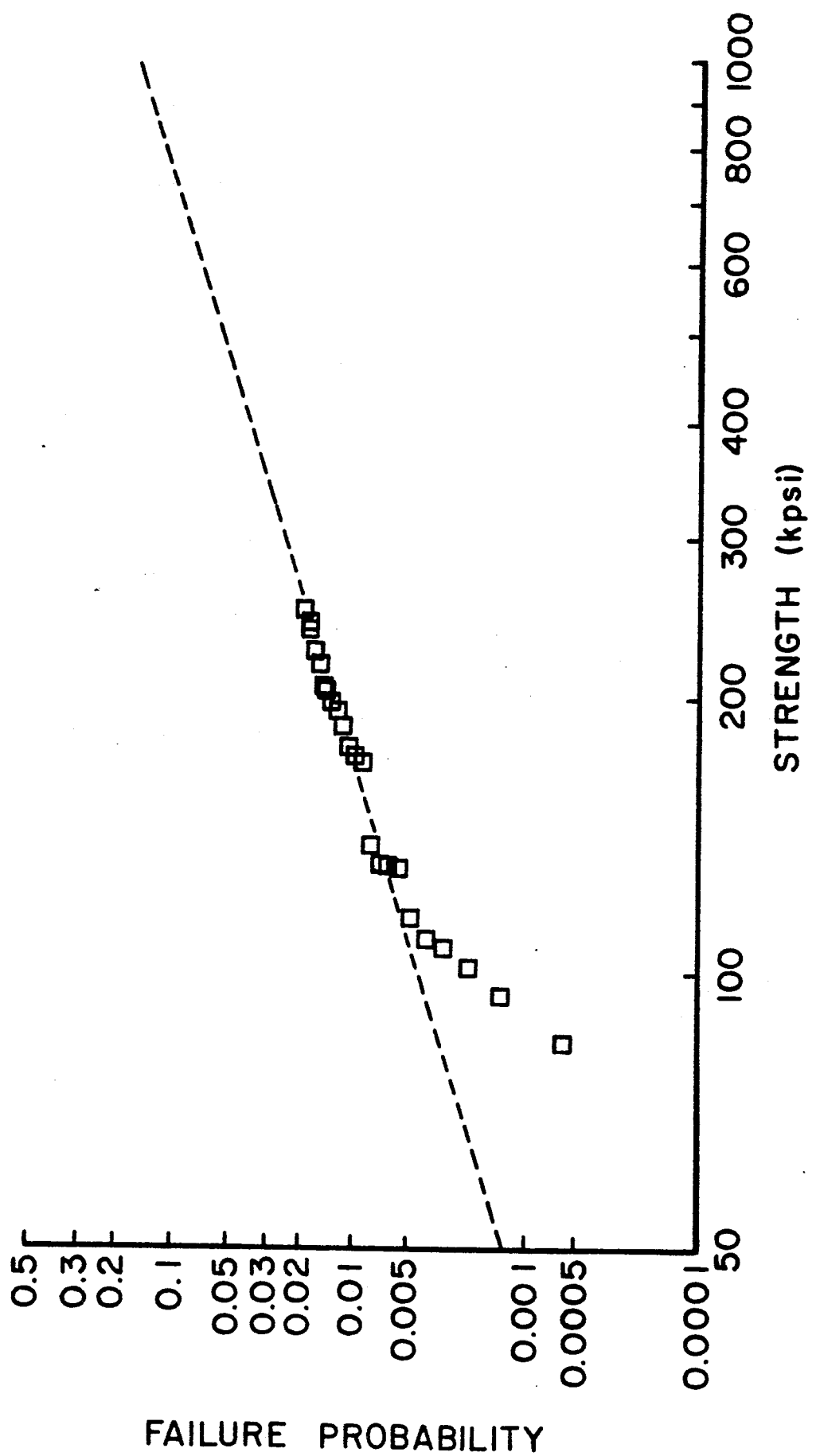
FIG. 8 is a graph characterizing the low end of the strength distribution for 24 kilometers of optical fiber.

Once twenty meters of optical fiber had been indexed and clamped in place, the load cell 41 increased its load from an initial value to 250 kpsi. The load cell 41 moved from its home position to its maximum position for each indexed length of optical fiber. The screener stopped for one of three reasons: a break, manual shut off, or end of reel. Each break was recorded, with an indication of actual load at failure and total length of optical fiber payed out at failure. In this example, the maximum level set corresponded to 250 kpsi stress. The graph of FIG. 8 depicts the probability of failure (1 = 100%) at each strength in kpsi for a 25 kilometer reel of optical fiber.

Although the present invention has been described with respect to a specific device, it is not intended that such specific references be limitations upon the scope of the invention which is defined as set forth in the following claims.

We claim:

1. A method of strength testing optical fiber comprising the steps of:
   (A) providing a payout reel which contains a length of optical fiber which is to be strength tested;
   (B) training a length of said optical fiber around at least a portion of the periphery of a first wheel so that the axis of said optical fiber is substantially perpendicular to the axis of said first wheel;
   (C) training said optical fiber around at least a portion of the periphery of a second wheel;
   (D) training said optical fiber around at least a portion of the periphery of a third wheel so that the axis of said optical fiber is substantially perpendicular to the axis of said third wheel;
   (E) restraining the movement of said optical fiber with respect to at least said first wheel or said third wheel;
   (F) subjecting the length of said optical fiber between said first and third wheels to a continuously increasing tensile stress, which does not exceed a predetermined maximum stress, while measuring a variable which is related to the tensile stress in said optical fiber;
   (G) if said optical fiber breaks, repeating steps (A)-(F);
   (H) if said optical fiber does not break, relieving the tensile stress in said optical fiber and rotating said first and third wheels until a new length of optical fiber extends between said wheels; and,
   (I) repeating steps (E) and (F).

2. The method claim 1 wherein, in step (E), movement of said optical fiber is restrained with respect to both said first wheel and said third wheel, and the tensile stress in said fiber is induced by moving said second wheel away from said first wheel and said third wheel.

3. The method of claim 2, wherein said variable is measured by a load cell associated with said second wheel.

4. The method of claim 3 wherein movement of said optical fiber is restrained with respect to said first wheel and said third wheel by preventing rotation of said wheels and clamping said optical fiber against the peripheries of said wheels which are in contact with said optical fiber.

5. The method of claim 2 wherein the movement of said optical fiber is restrained with respect to both wheels by training said optical fiber at least once around each of said wheels and preventing the rotation of said wheels.

6. The method of claim 5 wherein said variable is measured by a load cell associated with said second wheel.

7. The method of claim 1 wherein said tensile stress is induced by:
   (A) training said optical fiber at least once around each of said first and third wheels;
   (B) restraining the rotation of one of said first or third wheels; and,
   (C) rotating the other of said first or third wheels.

* * * * *